(12) United States Patent
Dobbie

(10) Patent No.: US 9,173,901 B2
(45) Date of Patent: Nov. 3, 2015

(54) COMPOSITIONS AND METHODS OF USING LAMELLAR BODIES FOR MODIFYING LINEAR BIOLOGICAL MACROMOLECULES

(75) Inventor: James Dobbie, Airdrie (GB)

(73) Assignee: LAMELLAR THERAPEUTICS LIMITED, Glasgow (GB)

(*) Notice: Subject to any disclaimer, the term of this patent is extended or adjusted under 35 U.S.C. 154(b) by 1151 days.

(21) Appl. No.: 12/313,724

(22) Filed: Nov. 24, 2008

(65) Prior Publication Data

US 2009/0111773 A1 Apr. 30, 2009

Related U.S. Application Data

(62) Division of application No. 10/827,172, filed on Apr. 19, 2004, now abandoned.

(51) Int. Cl.
| | | |
|---|---|---|
| *A61K 9/127* | (2006.01) | |
| *A61K 35/12* | (2015.01) | |
| *A61K 9/00* | (2006.01) | |
| *A61K 31/575* | (2006.01) | |
| *A61K 31/683* | (2006.01) | |
| *A61K 31/685* | (2006.01) | |
| *A61K 31/688* | (2006.01) | |

(52) U.S. Cl.
CPC .............. *A61K 35/12* (2013.01); *A61K 9/0043* (2013.01); *A61K 9/0046* (2013.01); *A61K 9/127* (2013.01); *A61K 31/575* (2013.01); *A61K 31/683* (2013.01); *A61K 31/685* (2013.01); *A61K 31/688* (2013.01)

(58) Field of Classification Search
CPC ..................................................... A61K 9/127
USPC ......................................................... 424/450
See application file for complete search history.

(56) References Cited

U.S. PATENT DOCUMENTS

| | | | |
|---|---|---|---|
| 5,006,343 A | | 4/1991 | Benson et al. |
| 5,262,405 A | * | 11/1993 | Girod-Vaquez et al. ........ 514/75 |
| 5,403,592 A | | 4/1995 | Hills |
| 5,462,752 A | | 10/1995 | Chao et al. |
| 5,643,599 A | | 7/1997 | Lee et al. |
| 5,877,273 A | | 3/1999 | Hance et al. |
| 5,925,375 A | | 7/1999 | Lenk et al. |
| 6,193,997 B1 | | 2/2001 | Modi |
| 6,290,987 B1 | | 9/2001 | Modi |
| 6,719,960 B1 | | 4/2004 | Hills et al. |
| 7,544,369 B2 | | 6/2009 | Boni et al. |
| 7,718,189 B2 | | 5/2010 | Boni et al. |
| 2002/0031543 A1 | | 3/2002 | Iwaarden et al. |
| 2004/0110695 A1 | | 6/2004 | Dobbie |
| 2004/0126420 A1 | | 7/2004 | Dobbie |
| 2005/0070877 A1 | | 3/2005 | Dobbie |
| 2009/0111773 A1 | | 4/2009 | Dobbie |
| 2010/0260829 A1 | | 10/2010 | Boni et al. |

FOREIGN PATENT DOCUMENTS

| | | |
|---|---|---|
| EP | 0976403 | 2/2000 |
| GB | 2335853 | 10/1999 |
| JP | H02-295933 | 12/1990 |
| JP | H03-501250 | 3/1991 |
| JP | H10-503199 | 3/1998 |
| JP | 2001-510162 | 7/2001 |
| WO | 89/01777 | 3/1989 |
| WO | 90/07469 | 7/1990 |
| WO | 91/12026 | 8/1991 |
| WO | 92/21981 | 12/1992 |
| WO | 9221981 | 12/1992 |
| WO | WO 92/21981 | 12/1992 |
| WO | 95/08986 | 4/1995 |
| WO | 96/03136 | 2/1996 |
| WO | 96/09059 | 3/1996 |
| WO | WO 96/09059 | 3/1996 |
| WO | 97/03703 | 2/1997 |
| WO | 9703703 | 2/1997 |
| WO | 97/13501 | 4/1997 |
| WO | 97/26889 | 7/1997 |
| WO | WO 97/26889 | 7/1997 |
| WO | 98/50527 | 11/1998 |
| WO | 9850527 | 11/1998 |
| WO | 98/53800 | 12/1998 |
| WO | 99/03481 | 1/1999 |
| WO | 99/33472 | 7/1999 |
| WO | WO 99/33472 | 7/1999 |
| WO | 99/51244 | 10/1999 |
| WO | 00/18371 | 4/2000 |
| WO | 00/69412 | 11/2000 |
| WO | 01/72277 | 10/2001 |

(Continued)

OTHER PUBLICATIONS

Post et al, Experimental Lung Research, vol. 3, pp. 17-28, 1982.*
King, et al., Bulk Shear Viscosities of Endogenous and Exogenous Lung Surfactants; *Amer. Journal of Physiology*; vol. 282; p. L277-L284; 2002.
Kobayashi, et al.,; Surfactant-like Substance and Otitis Media with Effusion; *Elsevier Science Publishers*; vol. 84; p. 15-19; 1995.
Ghadiali, et al., Effect of Surface Tension and Surfactant Administration on Eustachian Tube Mechanics; *Journal of Applied Physiology*; vol. 93; p. 1007-1014; 2002.
McGuire, John; Surfactant in the Middle Ear and Eustachian Tube; *Int'l Journal of Pediatric Otorhinolaryngology*; vol. 66; p. 1-15; 2002.
Nemechek, et al., Nebulised Surfactant for Experimentally Induced Otitis Media with Effusion; *Otolaryngology and Head and Neck Surgery*; vol. 117; p. 475-479; 1997.
Ma Jiangang, et al.,; Histopathological and Ultracytochemical Observation of Mucosa on the Eustachian Tube and Middle Ear with Experimental Secretory Otitis Media; *US Nat'l Library of Medicine*; vol. 17; p. 359-361; 2003.

(Continued)

*Primary Examiner* — Gollamudi Kishore
(74) *Attorney, Agent, or Firm* — Klauber & Jaskson LLC

(57) ABSTRACT

Compositions comprising therapeutically effective amounts of lamellar bodies for the modification of linear macromolecules are disclosed. These lamellar compositions are useful in the treatment of conditions or diseases characterized by a preponderance of heavy mucous secretions, such as otitis media, cystic fibrosis, bronchitis, sinusitis and nasal congestion. Methods of treating these diseases and conditions by administering a therapeutically effective amount of a composition to a patient requiring such treatment are also disclosed.

5 Claims, No Drawings

(56) References Cited

FOREIGN PATENT DOCUMENTS

| WO | WO 01/72277 A | 10/2001 |
|----|---------------|---------|
| WO | 02/24162 | 3/2002 |
| WO | 03/082245 | 10/2003 |
| WO | WO 03/082245 | 10/2003 |

OTHER PUBLICATIONS

Schmitz, et al.,; Structure and Function of Lamellar Bodies Lipid Protein Complexes Involved in Storage and Secretion of Cellular Lipids; *Journal of Lipid Research*; vol. 32; p. 1539-1570; 1991.
Post, et al.,; Lamellar Bodies Isolated from Adult Human Lung Tissue; *Biosis*; p. Whole Document; 1982.
Wang, et al.,; Ultrastructure of Surfactant-like Multilamellar Bodies in the Human Nose; *US Nat'l Library of Medicine*; vol. 36; p. 321-322; 2001.
Cevc Phospholipids Handbook, Marcel Dekker, title and copyright pages only (1993).
Dobbie, et al., Perit. Dial. Int'l 16:482-487 (1996).
Hite, Clin. Pulm. Med. 9:39-45 (2002).
Attwood, Science, vol. 290:471-473 (2000).
Skolnick, et al., Trends in Biotech, 18(1):34-39 (2000).
Metzler, et al., Nature Structrual Biol., 4:527-531 (1997).
Ghadiali, et al., J. Appl. Physiol, 93:1007-1014 (2002).
Jiangang, et al., J. Clin. Otorhinolaryngol, 17:359-361 (2003).
King, et al., Am. J. Physiol. 282:L277-L284 (2002).
Kobayashi, et al., Practica otolocia 84:(suppl): 15-19 (1995).
McGuire, Int'l J. Pediatr. Otorhinilaryngol, 66:1-15 (2002).
Nemechek, et al., Otolaryngology Head and Neck Surgery 117:475-479 (1997).
Ngo, et al., The Protein Folding Problem and Tertiary Structure Prediction, Birkhauser, pp. 492-495 (1994).
Post, et al., Exp. Lung Res., 3:17-25 (1982).
Schmitz, et al., J. Lipid Res., 32:1539-1570 (1991).
Wang, et al., Chinese J. Otolaryngology 36:321-322 (2001).
International Search Report for PCT/GBO1/01936, seven pages dated Apr. 5, 2002.
Masihi, et al, vol. 50:3:938-940; (1985).
Meyers, et al., "The immunological adjuvant activity and liposomes containing monphosphoryl lipid A and a synthetic analog of trehalose dimycolate." Federation of American Societies for Experimental Biology,1989 3(3): A605 XP002182355; ISSN: 0892-6638.

\* cited by examiner

COMPOSITIONS AND METHODS OF USING LAMELLAR BODIES FOR MODIFYING LINEAR BIOLOGICAL MACROMOLECULES

CROSS-REFERENCE TO RELATED APPLICATIONS

The present application is a division of U.S. Ser. No. 10/827,172, filed Apr. 19, 2004 which claims priority to UK application No. GB0322448.2, filed on Sep. 25, 2003, the disclosure of which is incorporated by reference herein in its entirety. Applicants claim the benefit of this application under 35 U.S.C. §119 (a-d).

FIELD OF THE INVENTION

The present invention relates to the identification of lamellar bodies which modify linear biological macromolecules that may be present in physiological and pathophysiological secretions and exudates, such as mucus, DNA, actin and bacterial-derived alginate, with respect to their physical properties, viscosity, adhesiveness, liquidity and three-dimensional disposition. The invention further relates to compositions and methods of treatment using these lamellar bodies.

BACKGROUND OF THE INVENTION

There are a number of occasions and sites where it would be beneficial to modify linear biological macromolecules, such as in disease states and during surgery. Examples where linear macromolecules are problematic are acute and chronic otitis media and sinusitis, acute and chronic inflammatory disorders of the respiratory tract (including cystic fibrosis), disorders of the alimentary and genito-urinary tracts, and during surgical procedures on ducts and surfaces of body cavities filled or covered by thickened secretions or exudates. There are no biologically efficacious substances or methods typically used for alteration or removal of these species of macromolecules, which in pathological situations can result in acute and chronic morbidity and mortality.

On the simple basis of observed viscosity or lubricity, older physiology texts classified secretions into thick or thin. Thick secretions were described as "mucoid", whereas thin secretions were considered "serous" in nature. These ill-defined archaic terms are still in use and have not been accurately defined and categorized. The term "serous" is applied to the sparse, thin secretions encountered universally in the large body cavities, pleura, pericardium, peritoneum, joints and tendon sheaths. This thin secretion is termed "serous" in that, like serum, it does not clot. In the last decade however, serous fluid in body cavities, was for the first time accurately defined as a secretion of mesothelium in which phospholipid microbodies were the predominant element in conferring high lubricity and non-stick properties (Dobbie J W, (1988) Ultrastructural similarities between mesothelium and Type II pneumocytes and their relevance to phospholipid surfactant production by the peritoneum In: Khanna R, Nolph K D, Prowant B, Eds: Advances in Continuous Ambulatory Peritoneal Dialysis. University of Toronto Press, Toronto, pp 32-41; Dobbie J W, Pavlina T, Lloyd J, Johnson R C. (1988); *Am J Kid Dis.,* 12:31-36; Dobbie J W, Lloyd J K. (1989), *Perit Dial Int,* 9:215-221). Subsequently it has been shown that not only mesothelium but many other tissues in respiratory, alimentary and reproductive tracts contain varying densities of "serous" cells, which secrete a similar substance.

Invisible to light and electron microscopy for so long, these findings have recently been responsible for the concept that the secretory system for these phospholipid microbodies constitutes a hitherto unrecognized major biological system throughout the animal kingdom (Dobbie J W. (1996) Perit Dial Int. 16:574-581).

Widespread throughout the animal kingdom, the secretion of mucus from body surfaces, in association with underlying motile projections of cell surfaces, cilia, together constitutes an important mechanical system for automatic clearance of potentially noxious substances. In lung, the mucociliary clearance system is the first line of defense against inhaled particulates, aerosols and pathogens, into its airways. Such materials are adsorbed out of the air stream onto the mucous gel contained within the airway surface liquid, which coats the ciliated epithelium. Despite the focus of intensive research in recent years, particularly in relation to the pathogenesis of cystic fibrosis, there remain unsolved biophysical problems in understanding the function of mucociliary clearance in all body surfaces. It is with respect to the identification of compositions for the treatment of diseases and conditions characterized by the preponderance of thick mucous secretions that the present application is directed.

SUMMARY OF THE INVENTION

The present invention relates to the discovery that lamellar body secretory cells are a biological necessity in sites where thick secretions such as mucus are produced, and in disease states where linear macromolecules possessing significant inherent visco-elastic and adhesive properties might be encountered.

It would be beneficial to provide a substance or method that is able to modify for therapeutic purposes linear macromolecules with respect to their physical properties in relation to viscosity, adhesiveness and rheological characteristics.

Accordingly, a first aspect of the present invention provides for a composition comprising a therapeutically effective amount of lamellar bodies for the modification of linear macromolecules. In a preferred embodiment, the composition is a pharmaceutical composition comprising the lamellar bodies and a pharmaceutically acceptable carrier. In another preferred embodiment, the pharmaceutical compositions may be used to treat a mammalian subject suffering from a disease or condition characterized by a preponderance of heavy mucous secretions and in need of such therapy. Such conditions include, but are not limited to, Otitis Media (acute or chronic), Cystic Fibrosis, sinusitis, bronchitis, and nasal congestion. In another preferred embodiment, the subject is a human. In another preferred embodiment, the lamellar bodies comprise about 44-70% phosphatidylcholine, about 15-23% sphingomyelin, about 6-10% phosphatidyl ethanolamine, about 2-6% phosphatidyl serine, about 2-4% phosphatidyl inositol and about 4-12% cholesterol by weight. In another preferred embodiment, the composition further comprises about 0-3% by weight of lysophosphatidyl choline. In a further preferred embodiment, the lamellar bodies comprise about 54% phosphatidylcholine, about 19% sphingomyelin, about 8% phosphatidyl ethanolamine, about 4% phosphatidyl serine, about 3% phosphatidyl inositol and about 10% cholesterol by weight. In another preferred embodiment, the composition further comprises about 2% by weight of lysophosphatidyl choline. In yet another preferred embodiment, the linear macromolecules in need of modification are selected from the group consisting of DNA, mucin, actin, and bacterial-derived alginate. These substances may be produced by the host or invading micro-organisms, i.e. they are substances produced or released by either prokaryotes or eukaryotes.

A second aspect of the present invention provides for a method of treatment for acute and chronic otitis media. In a preferred embodiment, the method of treatment comprises the steps of:
  a) inserting a needle through the tympanic membrane;
  b) introducing a composition including lamellar bodies through the needle into the ear; and
  c) allowing the lamellar bodies to modify the viscosity of the mucin in the ear such that it is capable of draining from the ear.

In another preferred embodiment, the method of treatment of otitis media comprises the steps of:
  a) inserting a needle through the tympanic membrane;
  b) introducing a composition including lamellar bodies through the needle into the ear; and
  c) allowing the lamellar bodies to modify the composition and the biological properties of the contents present in the pathological secretion, including linear macromolecules of the type mucus, DNA, actin and alginate, to the effect that the physical properties of the secretions such as viscosity and adhesiveness are altered, permitting therapeutic drainage of the middle ear.

In another preferred embodiment, the method comprises treating otitis media where a tympanostomy tube (vent tube) is in place and has become blocked by mucus or by an admixture of mucus and DNA, actin, alginate or wax, and comprises the step of introducing a composition including lamellar bodies into the external auditory canal.

In yet another preferred embodiment, the method of treatment for otitis media comprises the steps of:
  a) inserting a catheter into the pharyngeal opening of the Eustachian tube.
  b) introducing a composition, including lamellar bodies through the catheter into the ear.

Preferably the composition is introduced into the middle ear.

A third aspect of the present invention provides for a method of performing a functional endoscopic sinus surgical (FESS) procedure on the sinus or sinuses of a patient comprising the steps of:
  a) applying a composition including lamellar bodies to the sinus or sinuses;
  b) allowing lamellar bodies in the composition to modify the physical properties of viscosity and adhesiveness of linear macromolecules, including mucus, DNA, actin and alginate in the area of the sinus or sinuses such that the substances are capable of being removed; and
  c) introducing a surgical instrument into the nasal passage such as to remove tissue from the sinus or sinuses.

A fourth aspect of the present invention provides for a method for applying a composition including lamellar bodies to the respiratory passages to modify the physical properties of linear macromolecules of the type mucus, DNA, actin and alginate in pathologically altered secretions. The lamellar bodies modify the viscosity and adhesiveness of the secretions, increasing the fluidity of the airways' surface fluid and restoring mucociliary clearance of secretions throughout the respiratory tract.

In a preferred embodiment, the composition containing suspended lamellar bodies is introduced into the respiratory passages as an aerosol spray. In another preferred embodiment, the fluid containing suspended lamellar bodies may be subjected to ultrasonification during administration of inhaled aerosol. In yet another preferred embodiment, the therapeutic moieties can be included on or within the phospholipid bilayers which constitute the lamellar bodies for more effective access of therapeutic moieties to sequestered micro-organisms protected by prokaryote- and eukaryote-derived linear macromolecules.

A fifth aspect of the present invention provides for a method for applying a composition, including lamellar bodies, to diverse parts of the body for the symptomatic relief of viscous secretions in patients with the autosomol recessive disorder, cystic fibrosis, due to the gene defect responsible for the secretion of a protein called Cystic Fibrosis Transmembrane Conductance Regulator (CFTR). In a preferred embodiment, the method of symptomatic treatment of the pathological secretions in cystic fibrosis is accomplished by applying a composition containing suspended lamellar bodies which are introduced into the respiratory passages as an aerosol spray. In another preferred embodiment, the fluid containing suspended lamellar bodies may be subjected to ultrasonification during administration of inhaled aerosol. In yet another preferred embodiment, additional therapeutic moieties can be included on or within the phospholipid bilayers which constitute the lamellar bodies for more effective access of the therapeutic moieties to sequestered micro-organisms protected by prokaryote- and eukaryote-derived linear macromolecules. Another preferred embodiment provides for a method of symptomatic treatment of the effects of blockage of the secretory ducts of vital organs and glands in patients with cystic fibrosis by applying a composition including lamellar bodies through intermittent or continuous infusion into the drainage system by needles or appropriate macro- or micro-catheters, or introduction of slow-release matrices, enteric-coated or biodegradable capsules containing lamellar bodies.

Other advantages of the present invention will become apparent from the ensuing detailed description taken in conjunction with the following illustrative drawings.

DETAILED DESCRIPTION OF THE INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

Definitions

"Lamellar bodies or microbodies" as used throughout this document, refers to phospholipid, multilamellar, bilayered structures present in many tissues throughout the body, but also refers to the synthetic multilayered phospholipid structures having the novel composition described in the present invention. Thus, this term refers to both naturally occurring and synthetic lamellar bodies.

"Lamellasomes" as used herein refers to synthetically prepared lamellar bodies as described by the methods of the present invention.

"Serous" as used herein refers to an exudate or effusion that is thin and watery, and which lacks a significant cellular component.

"Treat", Treating" or "Treatment" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

A "therapeutically effective amount" is an amount sufficient to decrease or prevent the symptoms associated with the conditions or deficiencies contemplated for therapy with the compositions of the present invention.

"Slow release formulation" refers to a formulation designed to release a therapeutically effective amount of a drug or other active agent such as a polypeptide or a synthetic compound over an extended period of time, with the result being a reduction in the number of treatments necessary to achieve the desired therapeutic effect. In the matter of the present invention, a slow release formulation would decrease the number of treatments necessary to achieve the desired effect.

"Combination therapy" refers to the use of the agents of the present invention with other active agents or treatment modalities, in the manner of the present invention for treatment of otitis media or abdominal surgery. These other agents or treatments may include drugs such as corticosteroids, non-steroidal anti-inflammatory compounds, or other agents useful in treating or alleviating pain. The combined use of the agents of the present invention with these other therapies or treatment modalities may be concurrent, or the two treatments may be divided up such that the agent of the present invention may be given prior to or after the other therapy or treatment modality.

"Local administration" means direct administration by a non-systemic route at or in the vicinity of the site of an affliction, disorder, or perceived pain.

"Modify" or "modification of" means to alter the physical status of a material with respect to viscosity, adhesiveness and/or fluidity. In the present invention "modification" refers to changes in physical characteristics, perhaps due to changes in hydration of the gel, although other factors may play a role in modification of the physical state.

"Acute otitis media" is an inflammation of the area behind the eardrum (tympanic membrane) in the chamber called the middle ear. Acute otitis media is an infection that produces pus, fluid, and inflammation within the middle ear. Acute otitis media frequently occurs as an aftereffect of respiratory infections as the nasal membranes and eustachian tube become swollen and congested.

"Chronic otitis media" refers to a middle ear infection that may develop when infection in the middle ear persists for more than 2 weeks. The middle ear and eardrum may start to sustain ongoing damage occasionally resulting in drainage through a nonhealing hole in the eardrum.

Throughout this document the term "linear macromolecule" refers to molecules which are linear at the molecular level and whose structure essentially comprises the multiple repetition in linear sequence of units derived from molecules of low relative molecular mass. The molecules may possess side-chains, but these will not typically participate in chemical cross-linking. Examples of linear macromolecules of this species include mucus, DNA, actin and alginate.

"Therapeutic moieties" refers to any therapeutically effective molecule, whether it is a small organic chemical compound, or a protein or peptide, or a nucleic acid, or an antibody or antibody fragment, or a carbohydrate, that may be attached to the lamellar bodies and administered to subjects suffering from diseases or conditions for which treatment may be beneficial. Optionally, therapeutic moieties can be included on or within the phospholipid bilayers which constitute the lamellar bodies.

General Description

It was not until the time of the present invention that treatment of diseases having thick mucoid secretions with compositions containing the lamellar bodies of the present invention was contemplated. That is, a recent key advance in molecular biology and physiology has been the realization that the thin "serous" secretions which have high lubricity and do not form gels (clots), can exist on their own in body cavities, ducts, glands, surfaces, etc, whereas thick, "mucoid" secretions are in normal physiological states always accompanied by cells which secrete a serous solution containing phospholipid microbodies.

The invention described herein has provided new observations and explanatory concepts resulting in the conclusion that a biological agent which counteracts the viscosity of thick mucous secretions is always provided in the form of accompanying "serous" secretory cells. The likeliest function of phospholipid microbodies on gels consisting of tangled linear polymers would be the modification of their adhesive and visco-elastic properties.

Studies on the effect of synthetic lamellar bodies on the adhesiveness, viscosity and fluidity properties of mucous secretions has for the first time provided observations that the key constituents of "serous" secreting cells (lamellar bodies) significantly modify the physical properties of mucus. It has further been shown that synthetic lamellar bodies also have a significant effect on the physical properties of pathophysiological thick secretions, which contain polymeric DNA, actin or alginate derived from dead host cells and bacteria.

Therapeutic Uses and Compositions

Chronic Otitis Media with Effusion (COME)

COME is an extremely common condition, particularly in children. Following an acute or repeated acute attacks of otitis media, the middle ear may become filled with a viscous secretion referred to as "glue ear". This can become an intractable problem with serious consequences for hearing and in many cases, delayed or impaired speech and learning. Venting through grommets is the mainstay of present-day practice. There is widespread agreement among otolaryngologists that current methods of treatment are often sub-optimal in their outcome. Although much recent effort has been deployed into research to find better modes of treatment, it is unfortunate that only minimal attention has been paid to the little known finding of serous secreting cells in the Eustachian tube and middle ear.

Nature of the Epithelial Lining of the Middle Ear and the Eustachian Tube

The nature of the lining of the Eustachian tube and middle ear has for long been considered to be a "modified" respiratory epithelium containing both ciliated and goblet cells derived from the basal layers. However, based on investigations of whole mounted histological preparations from fetuses, premature infants, infants, normal children and adults, Tos concluded that mucous secreting cells are not a normal but a pathological component of middle ear epithelium (Tos M, Caye-Thomasen P, (2002), *J Oto-Rhino-Laryngology & Related Specialties.* 64:86-94). Indeed, it is now increasingly accepted that the lining epithelium throughout the Eustachian tube and middle ear in normal health, secretes but a sparse, thin solution which merely confers a glistening appearance to the membrane. The only cells likely to be responsible are loosely described in the literature as "serous" cells.

Aetiopathogenesis of Chronic Otitis Media with Effusion (COME)

It is now accepted that the key factor in the aetiopathogenesis of COME is the metaplastic transformation of middle ear epithelium to a predominantly goblet cell layer engaged in long-term hypersecretion of mucus. Recent research into the pathophysiology of COME has demonstrated a continuous chain of reactions precipitated by bacterial infection, where stimulation by endotoxins, together with pro-inflammatory cytokines (IL1β, TNFα, IL8, PAF) and growth factors (ErbB & HepGF) are not only powerful promoters of goblet cell hyperplasia, but also act as highly potent secretogogues of mucus.

Functions of Lamellar Body Secretory System

In pulmonary alveoli the prime function of lamellar bodies is the provision of surfactant phospholipids to promote gaseous exchange at the fluid-air interface, and to lower the opening pressure of alveolar walls during inspiration.

In mesothelial-lined cavities, we have shown the function of lamellar bodies to be that of lubrication and provision of a non-stick surface. This is achieved through the formation of microscopic, multilamellar ball and roller bearings which constantly form and reform between sliding surfaces.

In open body surfaces and ducts, upper respiratory, gastrointestinal and reproductive tracts, we have produced evidence that, in addition to conferring non-stick properties, a key function of lamellar body secretion in these sites is the modification and/or disaggregation of locally produced gels, such as mucus. This extremely important property is the biological guarantee that vital surfaces, ducts and tubes have a highly conserved method for preventing smothering and blockage by viscous secretions.

Lamellar Body Secretion in Middle Ear

In 1984 it was first demonstrated that the epithelial lining of the rat Eustachian tube synthesised phosphatidylcholine, the principal constituent of pulmonary surfactant, in amounts comparable to that produced by pulmonary alveolar epithelium (Wheeler S L, Pool G L, Lumb R H. (1984), *Biochim Biophys Acta,* 794:348-349). This was the first indication that the Eustachian tube epithelium produced a secretion with surfactant properties. Although this paper stimulated Dobbie et al (Dobbie J W, Pavlina T, Lloyd J, Johnson R C, (1988), *Am J Kid Dis,* 12:31-36) to apply their methodology to mesothelium, Wheeler's pioneering observations failed to evoke much interest or research in the otolaryngological community. In the last several years however, a small number of research papers on the ultrastructure of middle ear epithelium has confirmed by electron microscopy the presence of lamellar body secreting cells, so-called "serous" cells (Mira E, Bonazzo M, Galioto P et al. (1988), *J Autorhino Laryngology & Related Specialities,* 50:251-256.).

New Concepts on the Function of Phospholipid Secretion in Normal State and Pathological Conditions in Middle Ear A review of recent research carried out on the epithelial lining of the middle ear, considered in relation to our comparative ultrastructural and physiological research on lamellar body secretion at all other non-pulmonary locations, indicates that in the normal state, a constant thin secretion of lamellar bodies has a prime function in providing a non-stick surface in the Eustachian tube, tympanic cavity and air sacs, as we have demonstrated in the mesothelial-lined cavities of the body. In this site formation of adhesions, synechiae or outright blockage of the ductal portions of the system must be avoided at all costs. Thus it would have been surprising indeed if the benefit of highly conserved non-stick properties of lamellar bodies had not been present in these important cavities.

Like the upper respiratory tree, the middle ear, under the stimulus of inflammation, has the ability to produce mucous secreting goblet cells. However, current understanding of the physiology and pathophysiology of middle ear has not yet become aware of the dual, balanced system of mucus and lamellar body secretion.

The preparation of synthetic lamellar bodies now allows, for the first time, an opportunity to examine the interaction in a controlled ex vivo model, the possible physico-chemical interaction between phospholipid microbodies and naturally-occurring gels consisting of tangled networks of linear glycoprotein polymers.

"Surfactant" in the Middle Ear

In the last several years there has been a quickening of interest in the possible role of "surfactant" in the physiology and pathophysiology of the middle ear. The theme of the investigations has assumed that surfactants are in some way involved with ventilation, protection and clearance of the middle ear through the Eustachian tube. These functions have been examined by administration of exogenous surfactant and have successfully demonstrated that surfactant decreased the opening forces of the Eustachian tube, even in otologically healthy rats (Van Heerbeek N, Tonnaer E L G M, Koen J A O et al. (2003), *Otology & Neurotology,* 24: 6-10). In this capacity however, the lamellar bodies supplied in the surfactant are not functioning as a surfactant as such, but as a coating, which prevents adhesion of opposing surfaces. No significant effect however was observed on mucociliary clearance. In this respect there is an on-going failure to recognize that it is now established that the lubricating and non-stick properties of lamellar bodies constitute the major function of this system, and its pulmonary surfactant properties are a late, highly specialized evolutionary development. Similarly, it has not yet dawned on workers in this field that it would be a worthwhile experiment to mix these lubricating microbodies with gels of linear macromolecules such as mucus and DNA, which are pivotal in middle ear pathology.

This is not to deny the importance of the lamellar bodies' role as a surfactant in the gaseous exchange which occurs across the middle ear and associated air cells, and must play some significant part in ventilation. This well-known function of surfactant however, has blind-sighted researchers from investigating the more mundane role of lamellar bodies as a "biological lubricant and cleanser" of thick secretions.

Secretion of Lamellar Bodies by Serous Cells in the Mucosa of the Nasal Cavities and Sinuses It has recently been shown that there are scattered throughout these cavities serous cells which have been shown by electron microscopy to secrete typical lamellar bodies. In chronic infection, under the stimulus of endotoxins, exotoxins, and pro-inflammatory cytokines, there is a hyperplasia of goblet cells leading to excessive mucous secretion. These cavities are then liable to blockage and interruption of drainage due to thick secretions of viscous mucus, DNA, actin and bacterial-derived alginate.

Therapeutic application of lamellar bodies by aerosol spray typically will be used in disorders of the respiratory passages in which pathophysiological changes in the consistency of secretions due physical status of linear macromolecules are acute and chronic organismal-induced inflammation of the respiratory passages (acute and chronic bronchitis, bronchiectasis etc), acute and chronic inflammation induced by allergens (organic and inorganic) as in all types of asthma. Increased viscosity of secretions caused by inhalation of irritant or toxic particulate inducing alteration in the thickness of airway secretions as in for example, byssinosis due to inhalation of cotton dust and bagassosis, inhalation of bagasse (dried sugar cane refuse). The application of lamellar bodies will also be made to the respiratory passages to disperse extracellular polymeric substance (EPS), a protective biofilm secreted by diverse pathogenic micro-organisms, including *Pseudomonas aeruginosa*, in chronic respiratory disorders.

Use of Lamellar Bodies to Treat Cystic Fibrosis

The present invention also provides for a method for applying a composition, including lamellar bodies, to diverse parts of the body for the symptomatic relief of viscous secretions in patients with the autosomol recessive disorder, cystic fibrosis, due to the gene defect responsible for the secretion of a protein called Cystic Fibrosis Transmembrane Conductance Regulator (CFTR). This renders the cell membrane permeant to chloride and other larger organic anions. The condition is characterized by gross increases in the concentration and viscosity of mucus in the respiratory, alimentary, gastro-intestinal and reproductive tracts. Chronic, high density colonization of secretions by bacteria, leads to sequestration of high concentrations of polymeric DNA and actin from dead host leucocytes and bacteria which further thicken the secretions, paralyzing mucociliary clearance. Also, colonization by organisms which actively secrete protective biofilms including *Pseudomonas aeruginosa* which produce a viscous linear macromolecule (alginate), further thickening pathological secretions and creating physical barriers, rendering the organism inaccessible to chemotherapeutic attack. In cystic fibrosis, respiratory disease is the principal cause of mortality.

There are no biologically efficacious substances or methods typically used for modifying the physical properties these species of linear macromolecules which, in concert, are responsible for dysfunctional secretions in cystic fibrosis.

The present invention provides for a method of symptomatic treatment of the pathological secretions in cystic fibrosis by applying a composition containing suspended lamellar bodies which are introduced into the respiratory passages as an aerosol spray. Optionally, the fluid containing suspended lamellar bodies may be subjected to ultrasonification during administration of inhaled aerosol.

Optionally, therapeutic moieties can be included on or within the phospholipid bilayers which constitute the lamellar bodies for more effective access of therapeutic moieties to attack sequestered micro-organisms protected by prokaryote- and eukaryote-derived linear macromolecules.

Although pathological secretions in the respiratory tract are the principal cause of morbidity and mortality, their effect on other surfaces, passages and ducts results in significant lesions due to blockage and cyst formation particularly in the alimentary and genito-urinary tracts in patients with CF. As for the respiratory tract, there are no biologically efficacious substances or methods typically used in cystic fibrosis for modifying the effects of linear macromolecules in extrapulmonary sites.

The present invention also provides for a method of symptomatic treatment of the effects of blockage of the secretory ducts of vital organs and glands in patients with cystic fibrosis by applying a composition including lamellar bodies through intermittent or continuous infusion into the drainage system by needles or appropriate macro- or micro-catheters, or introduction of slow-release matrices, enteric-coated or biodegradable capsules containing lamellar bodies.

This method of symptomatic treatment is appropriate for ductal structures and passages throughout the entire body, including the surfaces of the gastro-intestinal tract with particular relevance to the thickened membrane covering the mucosa of the small bowel, pancreatic and hepato-biliary drainage network, the genito-urinary system, including intra-renal tubules, medullary drainage system, renal pelvis, ureters, bladder, bladder diverticula, urethra, vesico-colic fistula, ileo-vesicle fistula, vas deferens, seminal vesicles, prostate, cervix, endometrium, Fallopian tube mucosa, salivary and lachrymal glands.

Optionally, therapeutic moieties can be included on or within the phospholipid bilayers which constitute the lamellar bodies for more effective access of therapeutic moieties to sequestered micro-organisms protected by prokaryote- and eukaryote-derived linear macromolecules.

Basic laboratory testing of the effect of lamellar bodies (with the testing being carried our using synthetic lamellar bodies) on the adhesiveness, viscosity and fluidity properties of secretions has, for the first time, shown that the lamellar bodies significantly modify the physical properties of mucus. It has further been shown that synthetic lamellar bodies also have a significant effect on polymeric DNA and actin which can be derived from dead host cells and bacteria. Likewise, synthetic lamellar bodies have been shown to modify physical properties, including viscosity and adhesiveness of alginate of the type secreted by pathogens responsible for a range of life-threatening disorders.

Physical and Biological Properties of Mucous Secretions

Mucus is the archetypal slimy substance, which coats many epithelial surfaces and is secreted into fluids, such as airway surface fluid, saliva and gastro-intestinal juices. Mucus forms a layer adherent to epithelial surfaces of the respiratory, alimentary and genito-urinary tracts. There it acts to entrap micro-organisms, to provide a diffusion barrier against contact with noxious substances (e.g. inhaled smoke, gastric acid) and allegedly to serve as a lubricant to minimize shear stress damage to the delicate membranes.

Mucus is composed of polymeric glycoproteins suspended in water that contains electrolytes. It has an extended polypeptide backbone (apomucin), with numerous oligosaccharide side chains. Covered by abundant polyanionic charges, mucus, on exocytotic release from goblet cells, becomes extensively hydrated. Resistant to dehydration, it possesses unique rheological properties of high elasticity, adhesiveness and low solubility. Mucin monomers are polymerized through end-to-end disulphide bonds to form linear polymers which in respiratory mucus are at least 30μ long. Mucus forms a gel whose three-dimensional structure comprises a tangled network of linear mucin polymers devoid of intermolecular cross bridges. In airway surface liquid in normal individuals, mucin concentration is 1% by weight. In cystic fibrosis, an inherited respiratory disorder, mucin concentration is 3-4%.

Widespread throughout the animal kingdom, the secretion of mucus from body surfaces, in association with underlying motile projections of cell surfaces, cilia, together constitutes an important mechanical system for automatic clearance of potentially noxious substances. In lung, the mucociliary clearance system is the first line of defence against inhaled particulates, aerosols and pathogens, into its airways. Such materials are adsorbed out of the air stream onto the mucous gel contained within the airway surface liquid that coats the ciliated epithelium. The focus of intensive research in recent years, particularly in relation to pathogenesis of cystic fibrosis, there remain unsolved biophysical problems understanding the function of mucociliary clearance in all body surfaces.

Research work on mucus carried out by the inventor has revealed totally new insights into the functioning of mucus throughout the body. Data provided by these studies supports the hypothesis that where the mucociliary system is present it is invariably accompanied by an integrated parallel system whose secretory product modifies and controls the physicochemical, and biological properties of mucus. Through the unmasking of the hitherto unrecognized nature and importance of respiratory serous secretions as an essential part of the lamellar body secretory system, satisfactory explanations for anomalous observations and unsolved problems of the physics, molecular biology and pathophysiology of mucociliary clearance have been found.

Until now, mucous secretion has been viewed as a coherent, self-contained secretory system whose principal function is to provide a substance, which serves as the major protectant of epithelial surfaces throughout the body. Although recent research has demonstrated that the secretion of mucus by goblet cells is responsive to a very wide range of factors from organismal products, through cytokines to neural and hormonal stimuli, there has been no appreciation that a parallel system of secretory cells releases microbodies onto epithelial surfaces which have a profound modifying effect on the consistency, properties and disposal of mucus. This is the much neglected and poorly understood secretion of the serous cells that are always found in association with goblet cells.

It has long been recognized that throughout respiratory airways there were two cell populations in the surface epithelium, the predominant type being mucous secreting cells called goblet cells and the lesser known serous secreting. Whereas goblet cells release a thick or viscous secretion, serous cells were credited with the production of a thin watery solution. Mucous secretion has received by far the most attention from biological researchers, in comparison to the serous cells whose secretion has been largely ignored. The reason for the disregard lies in the unfortunate failure to identify accurately the nature of the secretion. This was due to the fact that tissue from the respiratory passages, fixed and processed using standard techniques for examination by electron microscopy, did not preserve the contents of the secretory vesicles within the serous cells which appeared to be empty. When however, the cells were fixed with tannic acid and glutaraldehyde, the vesicles are shown to contain osmiophilic phospholipid bilayers arranged in complex geometric patterns. These are lamellar bodies.

Of the few investigations carried out on serous cells, it was observed that those in the respiratory tree, sometimes called Clara cells, did produce phospholipid microbodies. However, the possibility that airways surface fluid contained a balanced mixture of thick, visco-elastic polymer and a highly efficient lubricant microbody has not been considered by research workers in this field. Indeed, the inventor has demonstrated that this dual partnership of mucus and lamellar bodies locally produces a combined and balanced solution with two ingredients with opposing physico-chemical properties. The body surfaces in the respiratory, gastro-intestinal and genitourinary tract contain cells that secrete mucus and cells that secrete lamellar bodies. The relative proportions of each type of cell varies from site to site according to the proximity to major, local changes in anatomy, e.g. sphincters, and in time and rate of secretion in response to physiological or pathological stimuli.

In conclusion, the recent discoveries of the inventor, using electron microscopy, of the ubiquity of lamellar body secreting cells and especially the demonstration that they are found in tandem with mucous secreting cells, has provided new insights into the existence of a balanced system which exercises control over the micro-environment of surfaces and ducts. As predicted by ultrastructural research on this recently discovered secretory system, the creation of synthetic lamellar bodies has provided for the first time in vitro confirmation of the modifying effect of lamellar bodies on the physical properties of secretions and exudates containing linear macromolecules.

DNA, Actin And Alginate In Pathological Secretions And Exudates

All of these substances are recognized as viscous molecules released in considerable amounts in a range of pathological processes, principally but not exclusively associated with organismal-induced inflammation. They may be involved usually with mucus, individually or in concert, in a conglomerate thickening of secretions or exudates in a variety of disorders, resulting in serious organ and tissue dysfunction through blockage of ducts and passages, including the Eustachian tube and middle ear in chronic otitis media, and in forming impenetrable layers on working surfaces.

There would appear to be a provision throughout the animal kingdom for the modification of the physical properties of these linear biological macromolecules.

DNA and Actin

DNA released from the nuclei of dead cells forms an extremely sticky substance. At a concentration of only 1%, polymeric DNA forms a solid gel in vitro. The volume of DNA released from dead leucocytes in an inflammatory process is considerable. Thus, sputum in cystic fibrosis may contain up to 10% DNA by weight. The linear macromolecule actin, principal constituent of the filamentous cytoskeleton, constitutes 20% of the total protein present in the average cell. This substance, likewise, is a viscous molecule which is released in significant amounts by dead leucocytes, further adding to the viscosity of inflammatory secretions and exudates. Additionally, both DNA and actin are released in not inconsiderable amounts from dead bacteria when present in infective processes.

Bacterial-derived Alginate

The bacterium, *Pseudomonas aeruginosa*, causes serious chronic infections throughout the body, including chronic otitis media, chronic sinusitis, and especially in the respiratory tract in patients with cystic fibrosis. Mucoid colonies of these organisms secrete an extracellular polymeric substance (EPS) known as exopolysaccharide alginate which significantly enhances their pathogenicity. The alginate is a straight-chain, hydrophilic, colloidal, polyuronic acid composed primarily of anhydro-beta-D mannuronic acid residues with 1-4 linkage. A viscous linear macromolecule, this alginate not only contributes significantly to the thickening of secretions colonized by the bacteria, but forms a biofilm which protects it from phagocytosis by macrophages.

These linear macromolecules constitute a serious hazard to drainage and clearance of secretions and exudates.

Surgical Procedures where Mucus, DNA, Actin and Alginate are a Problem

In many disease states the overproduction of mucus often occurs and is particularly problematic when surgical procedures are to be carried out. In most sites and conditions the overproduction of mucus is accompanied by pathological production and release of linear macromolecules (DNA, actin, alginate). Even in cases where mucus production is normal it can still be obstructive in surgical procedures.

Functional Endoscopic Sinus Surgery (FESS)

FESS is a minimally invasive procedure for the treatment of chronic sinusitis. It is designed to remove blockage and provide free drainage of the sinus. FESS causes little tissue damage and there is no visible scarring that is associated with open surgery. FESS is often recommended in cases of chronic sinusitis that do not respond well to medication or other forms of treatment. This occurs when the sinuses are blocked and unable to drain the mucus. When this happens, the sinuses can become infected.

The FESS procedure uses an endoscope, which enables the surgeon to identify and correct anatomic causes of sinus outflow obstruction. Other surgical instruments may be inserted alongside the endoscope to treat problems inside the sinuses. The kind of surgery will depend on the extent of the sinus problem. Sometimes other nasal procedures may be performed with the sinus surgery to improve access and drainage of the sinuses. In the present case we are suggesting that lamellar bodies or synthetic lamellar bodies can be used to modify the mucus prior to or during the procedure.

Typically the Procedure will Include the Steps of:
applying a composition including lamellar bodies to the sinus
allowing the lamellar bodies in the composition to modify the viscosity of the mucus and any admixed linear macromolecules such as DNA, actin or alginate in the area of the sinus such that it is capable of being removed
introducing a surgical instrument to the nasal passage such as to remove tissues from the sinus The amount of lamellar bodies in the composition is variable but typically the dosage concentration of lamellar bodies in the composition will be $10 \times 10^9$ per ml. The composition can take the form of a spray (nebulized, with and without ultrasonification), an injection or a slow-release preparation.

Other Surgical Areas

As well as being useful in ear, nose and throat procedures such as FESS and surgical treatment of Otitis Media, lamellar bodies can also be used in tract and ductal surgery where the secretion of mucus with or without admixtures of linear macromolecules such as DNA, actin and alginate, can make the procedure more difficult. Most commonly this will be applicable in surgery of the hepato-biliary ducts and gall bladder, pancreatic surgery, liver surgery, tracheal surgery, reproductive tract surgery, surgery of the salivary and lachrymal glands, including flushing of ducts, and surgery or descaling of the gastro-intestinal tract (in the cases the term surgery relates to procedures that will typically be carried out by a surgeon).

Fistula and Pathological Sinuses

"Fistula" is a term which describes the formation of an abnormal passageway which develops due to a pathological process. A fistula is usually a narrow tube lined not with an epithelial surface but with granulation tissue, which connects two body surfaces, either between two hollow viscera or between a hollow viscera and a body surface. Examples of this are a fistula which develops between colon and urinary bladder (vesico-colic fistula), and vagina and colon (vagino-colic fistula). Such lesions are notoriously difficult to eradicate and give rise to persistent focal, chronic and acute-on-chronic inflammation. Intermittent blockage and/or loculation of the fistula's lumen by thickened secretions of varying admixtures of mucus, DNA, actin and alginate are the key players in its maintenance and create serious obstacles to its surgical removal and closure. Instillation of topical antibiotics has minimal effect, due to blockage and coating of the fistula wall by thickened, impenetrable secretions. What is currently unavailable to surgeons is a biologically effective substance which will cleanse the fistula of the secretions harboring bacteria, endotoxin, pro-inflammatory cytokines and provide a period of continuous drainage to allow suppression of the inflammation in the wall of the fistula and clearance of pathogenic bacteria to permit successful surgical excision of the fistula's tract. Fistula are typically encountered in chronic inflammatory bowel disorders, including Crohn's disease and ulcerative colitis.

In the present case it is suggested that lamellar bodies or synthetic lamellar bodies can be used as a preparatory treatment as an adjunct for successful surgical treatment or eradication of pathological sinuses and fistulae. Typically, the procedure will include endoscopy of the affected viscera or organ to gain access for inserting a catheter into the sinus tract for applying a composition, including lamellar bodies, thereby introducing a flushing solution containing lamellar bodies or introduction of slow-release matrices, enteric-coated or biodegradable capsules containing lamellar bodies.

Other Treatment Areas where Modification of Mucus is Therapeutic

In a wide range of disorders, secretions may become so thickened that, rather than protecting surfaces or ducts, their viscosity causes severe local functional derangement. The pathophysiology responsible for the alteration in physical properties of the secretions is only partially understood. A prime cause of thickened mucous secretion is stimulation by endotoxins and cytokines, resulting in a proliferation of cells that secrete mucus. It is also recognized that the degree of hydration of mucus has a significant effect on its viscosity (particularly in cases such as cystic fibrosis).

Radiation-induced Mucositis

Following radiation therapy of the head and neck, areas of the nasopharynx, pharynx, larynx and trachea may exhibit a troublesome inflammation of the epithelial surfaces, resulting in thick exudates and secretions. These viscous, adhesive membranes harbour bacteria, endotoxins and pro-inflammatory cytokines which promote and prolong chronic inflammation at these sites, preventing healing. There is provided a method for applying a composition including lamellar bodies in a variety of forms including aerosol spray with or without ultrasonification, a suspension or gel to the areas affected by mucositis for the dispersement of the adhesive membrane, promoting healing of the inflamed areas.

Sinusitis

Sinusitis are membrane-lined openings in the bones around the nose. Four pairs of sinuses are connected to the nasal cavity by small openings and these sinus cavities rest alongside the nose, above the eyebrows and behind the cheekbones.

Normally, air passes in and out of the sinuses and mucus drains from the sinuses into the nose. When there is an obstruction, fluid is unable to pass through the sinuses freely. When sinuses are infected, membranes become swollen as blood rushes to the infected area. This swelling causes congestion, facial pain and increased mucus production. As a result, the nose may become runny and drippy. The mucous secretions may thicken over time creating a breeding ground for infections.

Acute sinusitis typically follows a cold and lasts for a few weeks. In the case of chronic sinusitis, the sinusitis may recur a number of times over the year. Typically, antibiotics and decongestants are used to treat the condition, although in the case of chronic sinusitis additional treatment methods are also often used.

In the present invention, it is suggested that a composition containing lamellar bodies can be used to treat sinusitis. The composition could take any form but typically would be in the form of a spray or nebulized formulation. As lamellar bodies modulate the viscosity of mucus this would help to relieve the symptoms of sinusitus. It can also be seen that a similar or the same formulation could be used to treat symptoms of the common cold or influenza. This would be particularly useful in the form of a nasal spray.

Cystic Fibrosis

Cystic fibrosis (CF) is the most common, lethal, autosomal recessive disorder in people of European extraction, affecting one in four thousand infants born per annum in the United States and Canada. Patients with CF die at an early age of respiratory failure due to profound lung injury secondary to colonization by pathogens and chronic inflammation of pulmonary tissues. The median survival age in North America for patients with CF had by 1996 reached thirty, whereas in South America it was nine years. Thus socio-economic conditions and availability of resources determine whether or not patients receive optimal care. These factors play an important role in the morbidity and longevity of individuals with this disorder.

The genetics of CF are now relatively well-understood. As an autosomal recessive disorder, both parents of an affected infant must carry the gene, and each pregnancy carries a one in four chance of producing a child with CF. The carrier rate in Europeans and their descendants is about one in twenty-eight, with the rate in other ethnic groups generally being lower. In 1989 the gene responsible for CF was located on the long arm of chromosome 7. Mutations cause either deficiency or absence of a membrane-spanning glycoprotein responsible for the maintenance of the ion channel which allows efflux of anions through the cell membrane in epithelium throughout the body. The protein is called the Cystic Fibrosis Transmembrane Conductance Regulator (CFTR). This channel renders the cell membrane permeant to chloride and other larger organic anions such as reduced glutathione (GSH). Despite this knowledge, there is however, a missing linkage between the genetics and the resultant pathology in CF.

The CFTR gene is found in epithelial cells of the respiratory, intestinal, hepato-biliary and reproductive tracts. It is also found in exocrine glands such as the serous glands in lung and in pancreas. Absence or dysfunction of the CFTR protein results in thick, viscous, mucous secretions in sinuses, lungs, biliary cannaliculae, intestines and epididymis, resulting in bronchiectasis, chronic liver disease, biliary and intestinal obstructions, infertility, pancreatic insufficiency and diabetes.

The essential pathological features of CF can be explained through blockage by viscous secretions of the cannaliculae, ducts and passages in tissues and organs where the lining epithelia are affected by the genetic deficiency. This results in progressive cyst formation, chronic inflammation and infection which weakens then destroys the walls of the ducts and passages, typically as encountered in bronchiectasis and pulmonary fibrosis, which are responsible for the greatest threat to life. Nevertheless, current research acknowledges the existence of a missing linkage between the genetics, its molecular expression and the pathogenesis of the lesions in the different tissues which characterizes CF as a defined disorder.

When it was discovered that the CF gene was responsible for the CFTR protein which controlled a chloride channel, its role in controlling the volume and electrolyte composition of sweat was established. Thus it was naturally assumed that a similar dysfunction in lung could explain the increased viscosity of the mucus via the hypothesis of abnormal salt concentration and low volume of airway surface fluid. Unfortunately, most evidence to date indicates that airway surface fluid is isotonic and of normal volume. Since electrolytes together with colloids are the key determinants of water distribution in tissue spaces, it was realized that the effect of the CFTR protein must be responsible for deficiencies other than electrolytes in the micro-environment within ducts and on surrounding epithelial surfaces. Therefore, in a continuing search for a molecular linkage between the gene defect and the resultant pathology, deficiencies of other anions have been sought. Of these, the ubiquitous tripeptide, reduced glutathione (GSH), one of the body's most important water-soluble anti-oxidants, has been considered a candidate for the missing linkage. GSH is present in extracellular epithelial fluids such as the airway surface fluid, gastro-intestinal juices, semen, etc. In the extracellular milieu, GSH provides powerful anti-oxidant protection to surfaces heavily exposed to reactive oxygen species, as in the lung airways where its concentration is 140 times the normal level in blood plasma. However, despite these actions of GSH, most workers in the field are of the opinion that they provide only a partial explanation for the resultant pathology.

In conclusion it is openly acknowledged by research workers that the true nature of the pathophysiology of CF is unknown and that the search should be extended for a missing factor or factors.

There is no single therapeutic procedure which successfully prevents the ultimate progression of the pathologies which result in death. The major effort in the treatment of CF is devoted to combating broncho-pneumonitis. The objective is to minimise tissue damage by facilitating bronchial clearance of viscous, infected mucus (chest physiotherapy, broncho-dilators, mucolytics), and reducing bacterial burden (antibiotics).

Although the pathophysiology is not yet understood, viscous mucus in CF lungs is acknowledged as being a major factor in the pathogenesis of the lesions. Recently, it has been realized that DNA, actin and *P. aeruginosa*-derived alginate play a significant aggravating role in thickening secretions and exudates in CF. There is thus an ongoing strategy to investigate the role of such substances in pathological secretions in CF and thereby to develop agents based on this premise to alleviate some of the features of airway obstruction.

The first product to reach the marketplace as a result of this strategy is recombinant human DNAse (rhDNAse). It is well-established that infected secretions in CF lungs contain as much as 10% DNA as a result of the continual breakdown of bacteria and neutrophils in chronically infected lungs. Extracellular DNA forms long molecular chains which increase the visco-elasticity of the secretions. RhDNAse alters the physical properties of CF secretions both in vitro and in vivo. Currently, some 50% of CF patients in the USA receive rhDNAse and it has been demonstrated that patients cough less and have less thick sputum. Its impact on lung function, however, is small. Young patients with mild lung disease given a six months course of rhDNAse produced only a 3% benefit in FEVI, but it decreased the frequency of intravenous antibiotic courses by 34%.

Another compound believed to have the potential to decrease sputum viscosity is gelosin, which breaks down polymeric filamentous actin (F-actin), another component in the thick secretions which makes an important contribution to its viscosity. Although polymeric F-actin makes up around 10% of CF sputum, clinical studies on the efficacy of gelosin have to date been disappointing.

With respect to patient tolerance of both agents, studies have shown that gelosin and DNAse may activate inflammatory mediators such as Interleukin 8, and may explain the disappointing impact of these compounds on lung function.

A further new approach to thinning thickened secretion in CF patients is the use of low-dose macrolide antibiotics, which interferes with the ability of pseudomonads to manufacture alginate, a major component of the protective coating of these bacteria. When these bacteria reach a critical density, they produce large quantities of alginate, creating a biofilm which interferes with the penetrance of antibiotics, access of acute inflammatory cells to the bacteria and hinders the clearance of the thickened secretions from airways in CF patients.

Separate products have therefore been individually developed with a view to facilitating the clearance of mucus, DNA, actin and bacterial-derived alginate in the grossly thickened secretions in CF patients with only relative success.

In the knowledge that lamellar bodies are secreted by serous cells in the airways, and in light of the fact that it has been shown by Applicant that lamellar body secretion in extrapulmonary sites is responsible for lubrication of serous cavities throughout the animal kingdom, ex vivo investigation of the effect of synthetic lamellar bodies on mucus, DNA, actin and bacterial-derived alginate was carried out. As demonstrated herein, the results confirmed that synthetic lamellar bodies significantly decrease the viscosity of mucus, polymeric DNA, actin and alginate in in vitro studies.

Therefore synthetic lamellar bodies possess the ability, as shown in vitro, to alter the viscosity, adhesiveness and fluidity of the individual and combined components of the thickened secretion in CF patients, in contrast to current therapeutic endeavours which have been directed at formulating specific agents for each component involved in the pathological process.

Accordingly, the inventor maintains that CF may be treated by exposure of the composite, pathologically thickened secretions to synthetic lamellar bodies. This will be achieved by restoration of adequate local levels of lamellar bodies, sufficient for the diminution of viscosity and adhesiveness, while increasing the fluidity and clearance of pathological secretions.

Furthermore, the inventor maintains that in CF a key factor in the pathogenesis of the disorder is relative failure of the lamellar body system to secrete adequate volumes of phospholipid microbodies to balance the physical properties of mucus and the pathological debris produced by intercurrent local inflammation (DNA, actin and alginate). Thus therapeutic effect is achieved by regular intermittent application of lamellar bodies to the affected tubal systems and surfaces, where the lubricating microbodies, as has been demonstrated in vitro, penetrate with ease the interstices of the gel-like structure of the thickened secretions.

Other Disease States

There are a number of other disease states in which linear macromolecules are central to their pathogenesis and progression of the condition in a manner outlined in detail in cystic fibrosis, where lamellar bodies or a lamellar body composition could be used to beneficial effect. These include respiratory disorders such as bronchitis and chronic bronchitis, asthma, bronchiectasis and chronic obstructive pulmonary disease. Additionally, disorders affecting the gastro-intestinal, hepato-biliary, pancreatic and reproductive tracts are subject to organismal and auto-immune induced thickened secretions. A variety of wounds affecting skin, such as thermal and radiation burns, chronic ulcers and de-gloving injuries with extensive loss of epidermis, dermis and full thickness skin, share a common pathological feature of adhesive and viscous exudates. Likewise, these constitute conditions where lamellar bodies or a lamellar body composition, could be used to beneficial effect.

The Skin: Lamellar Bodies in the Treatment of Thermal and Radiation Burns, in Chronic Ulcers and in Wounding Involving Extensive Loss of Epidermis, Dermis and Full Thickness Skin In burning injuries to skin, areas of loss of epidermis and dermis, down to full thickness skin, present a raw wound which is typically covered by viscous, highly adhesive exudates consisting of DNA and actin released from the nuclei of host-derived dead epidermal and dermal cells, leucocytes and pus cells, together with DNA and actin released from dead colonizing bacteria. The viscosity and adhesiveness of the exudates in many instances are further increased with the onset of significant infection by alginate-secreting organisms such as *Pseudomonas aeruginosa*, a frequent and troublesome infection in burns injuries.

The viscous and adhesive properties of the burns exudates give rise to several key pathological effects, which seriously compromise wound healing. The most damaging effect of the exudates is its tenacious adherence to wound dressings of all types and textures. Each time dressings are removed, the wound surface is traumatized, resulting in an out-pouring of fresh fibrin. This not only causes the patient extreme pain but also, this regularly repeated insult creates stratified layers of dense fibrin which seriously retard the healing process and are pathogenetically responsible for over-production of collagen and consequent scarification and deformity.

The viscous and adhesive burns exudate also impedes and restricts the ingress and movement of cells essential for the scavenging of debris, the phagocytosis of bacteria and cells involved in structural repair and re-epithelialization.

The viscous exudates, DNA and actin, provide sanctuary areas which foster infection, while colonization by organisms which actively secrete biofilm (alginate) then further augment the pathological effect of viscosity and adhesiveness. This sequential process progressively shields the colonizing organisms from attack by phagocytic cells and seriously restricts the penetration of antibiotics into the constantly thickening exudate.

It should be noted that lamellar bodies are normally produced in human skin by the keratinocytes. We have shown that in cell culture, replicating immature human keratinocytes vigorously secrete lamellar bodies. Although the scientific community has not yet considered the role of lamellar bodies in the promotion of wound healing, our detection by electron microscopy of their presence in skin and peritoneal wounds, strongly indicates the appropriateness of topical administration of lamellar bodies to wounds, particularly in burns, where the pathological presence of viscous and adhesive linear macromolecules seriously compromises healing and repair.

Chronic Skin Ulcers

A diverse range of chronic ulcers are encountered in skin. This occurs most commonly in lower limb and foot, particularly in diabetes mellitus, venous stasis and peripheral vascular disease. As with burns injuries, viscous and adhesive exudates consisting of DNA, actin and bacterial-derived alginates when present as a film on the surface of the ulcer base can seriously impair wound healing. This is a major factor in the maintenance of chronicity in ulcers of this type. As in the standard treatment of burns, adhesion of occlusive dressings to the ulcer base results in continual micro-trauma to the delicate membrane each time they are removed. This process therefore causes repeated episodic oozing of fresh fibrin over the base of the ulcer. Since fibrin is the major stimulus to production of granulation tissue, frequent episodes of fibrin exudation create a permanent state of earlystage wound repair in the base of the ulcer, which effectively blocks the natural progression to resolution and re-epithelialization.

Wounding Involving Extensive Denudation of Epidermis, Dermis Down to Full Thickness Skin (De-Gloving Injury)

Loss of skin in injuries of this nature creates a form of wound not dissimilar to that caused by burning. Likewise, occlusive dressings adhere tenaciously to the range of viscous molecules present in the surface exudate. Frequent or daily stripping of occlusive bandages provokes episodic exudation of fibrin, resulting in similar pathological sequelae encountered in burns and chronic ulcers.

Methods of Therapeutic Application

The following methods are applicable for diverse types of wounds, burns, chronic ulcers, de-gloving injuries. Wounds are sprayed with a suspension of lamellar bodies or a lamellar body composition before the dressings are applied. Preferably dressings should have micro-perforations of a diameter sufficient to allow passage of lamellar bodies through into the underlying wound. Likewise, the density of the pores per unit area shall be appropriate to adequate delivery of lamellar bodies to the underlying interface between the dressing and the wound when a suspension of lamellar bodies are sprayed over the outer surface of the dressing. The perforations on the dressings preferably should be of a density which does not compromise the occlusive properties of the dressing with respect to ingress of bacteria. At an appropriate time interval before its removal, dependent on the rate of delivery of lamellar bodies to the wound surface, the dressing will be sprayed with a suspension of lamellar bodies, which passes through the perforations into the space between it and the wound surface.

Dressings Incorporating Lamellar Bodies

A further method of application is the provision of dressings incorporating lamellar bodies which are released gradually from the under surface of the dressing onto the wound surface. This may be achieved by their containment in a thin envelope within the dressing, which acts as a reservoir for slow release of lamellar bodies through microscopic perforations by incorporating a porous membrane on the inner surface.

Lamellar bodies may also be incorporated in a dressing whose under surface is coated with a matrix or a gel from which they are released. Biocompatible gels would include hyaluronan and/or chondroitin sulphate. These gels are of lower viscosity compared to the pathological exudates present in wounds against which the lamellar bodies are directed, and the presence of lamellar bodies would confer a fluid, non-stick surface at the interface between wound and dressing.

Use of Lamellar Bodies in Disorders of the Mucous Membranes (Mucositis)

Inflammation of mucous surfaces, particularly those close to the body openings (buccal cavity, oropharynx, larynx, male and female genito-urinary tracts, and anal canal) are subject to painful inflammation, erosion and ulceration. A generic term, mucositis, denotes a not uncommon affliction caused by a wide spectrum of etiological factors, ranging from radiation, chemotherapeutic agents, drugs, auto-immunity, to allergies and infections. A characteristic feature of these conditions is the dryness of the surfaces, which become covered with sticky exudates consisting of viscous mucus, viscous DNA and actin from dead cells and bacteria. In extreme cases, opposing surfaces adhere one to the other forming synechiae, as in the oropharynx, prepuce, labia and vagina. Swallowing or slight movements affecting the surfaces are very painful. Separation of opposing surfaces causes repeated microtrauma to the mucous membrane such as to promote ulceration and prevent healing. Specific dermatological disorders, which give rise to these problems include Stevens-Johnson syndrome, Pemphigus, Behcet's disease, systemic lupus erythematosis and other bullous disorders. A suspension of lamellar bodies in physiological saline applied by regular spraying of the affected areas, or the application of lamellar body-containing gels or matrices will restore lubricity and non-stick properties to the dry, adherent surfaces. Application of lamellar bodies to affected mucous surfaces will decrease viscosity of the pathological secretions and exudates, solubilized crusting and prevent formation of synechiae.

Use of Lamellar Bodies in inflammatory Conditions of the Eye

Lamellar bodies are found in tears. We have shown by immunocytochemistry using the monoclonal antibody that the lacrimal epithelia stain positively for surfactant protein A. This indicates that lamellar body secretion is a constitutive function of lacrimal glands in man. The mucous membrane of the eyelids and the conjunctivae are normally moistened by a thin fluid. In pathological conditions the external surfaces of the eye may become dry and/or covered by thickened viscous secretions or exudates. These exudates may form crusts whose abrasive effect further excoriates and traumatises the inflamed surfaces. A wide variety of disorders give rise to lesions of this nature. In the common autoimmune disorders, rheumatoid and Sojgren's syndrome, an irritating dryness of the eyes called kerato-conjunctivitis sicca is a frequent occurrence. A wide variety of other disorders, inflammatory disorders due to viral or bacterial infection, allergies, adverse drug reactions give rise to blepharitis and conjunctivitis with accompanying viscous secretions and exudates. Regular administration of suspensions of lamellar bodies as eyedrops would be an appropriate therapeutic strategy whose usefulness and biocompatibility would be ascribed to the restorative effect of natural tears. Lamellar bodies may also be applied in the form of gel, matrices or slow-release devices or excipients.

Production of Synthetic Lamellar Bodies

The focus of the present invention is the therapeutic use of lamellar bodies. The following information provides details of their production and the key features and composition, which characterizes them as a novel microbody. In contrast to liposomes, whose invention from the outset was not based on a concept in any way related to a naturally-occurring microbody, synthetic lamellar bodies are designed to mimic a range of biological activities ascribed to naturally-occurring lamellar bodies in tissues and body cavities. The principal differentiating characteristics of naturally-occurring lamellar bodies are:

1) On contact, lamellar bodies, both divide easily and fuse readily one with the other in body cavities and tissues when subjected to movement and shear stress.
2) The provision of lubricity.
3) The automatic surface adsorption of planktonic molecular debris arising from inflammatory processes, etc.
4) The automatic, non-receptor-mediated endocytosis of lamellar bodies by the monocyte/phagocyte system, (and most especially by antigen presenting cells, dendritic cells and macrophages).

These properties are crucially dependent on the nature of the mix of the different species of phospholipids (phosphatidylcholine, sphingomyelin, phosphatidylethanolamine, phosphatidylserine and phosphatidylinositol) and the nature of their fatty acid chains whose heterogenicity, length and range of saturation and unsaturation leading to lamellar fluidity is of key importance for their striking range of biological activities.

In contrast to lamellar bodies, liposomes must on no account split or fuse. This is achieved by their different composition, conferring a necessary rigidity through high proportions of cholesterol and use of more rigid phospholipids which, together greatly reduces membrane fluidity. Liposomes are not designed to confer lubricity. The composition of liposomes is chosen not to confer any surface adsorptive properties, a feature which would be totally incompatible with liposomal usages. Liposomes are specifically designed not to be phagocytosed by the monocyte/phagocyte system, which would preclude any form of organ-targeted drug delivery which has been their prime, relatively unsuccessful use. Hence the development of Stealth liposomes in an attempt to obviate the biologically incompatible inherent paradox in the current formulation of liposomes.

The principal phospholipid constituents of lamellar bodies are phosphatidylcholine (PC), sphingomyelin (SPH), phosphatidylethanolamine (PE), phosphatidylserine (PS), phosphatidylinositol (PI) and lysolecithin (LPC). The phospholipid composition of lamellar bodies shows slight variation according to the cell of origin.

PC is the principal phospholipid in lamellar bodies, irrespective of site of origin. The percentage PC concentration varies from around 70% in lung lavage to 45% in synovial fluid (Refs). The next phospholipid in ranking concentration is SPH (15-23%). Thereafter, PE, PS, PI, PG and LPC are present in varying, single digit percentage concentrations in lamellar bodies according to site of origin.

The preferred composition of phospholipids and cholesterol for phospholipid multilamellar microbodies comprises: PC 54%:SPH 19%:PE 8%:PS 4%:PI 3%:cholesterol 10%. These values are median and the following range of compositions have been found in natural lamellar bodies (private research): PC 44-70%, SPH 15-23%, PE 6-10%, PS 2-6%, PI 2-4%, Cholesterol 4-12%. These figures are percentage by weight.

LPC may also be incorporated into the multilamellar microbodies at 2% by weight which follows the range found in natural lamellar bodies of 0-3%.

Liposomes are made by those skilled in the art with high cholesterol concentrations to improve their rigidity. Liposomes containing cholesterol at 20% or below would be considered to be cholesterol poor. Thus liposomes incorporating a high ratio (50%) of cholesterol, where it is equimolar with the phospholipids, have a highly stable structure and are the pivotal concept for the creation of liposomes. Until this invention, it would not to our knowledge have been obvious to try using low-cholesterol multilamellar microbodies since the late discovery of lamellar bodies as a ubiquitous biological phenomenon remains unknown and unquoted by anyone working in the liposomal field. The cholesterol content of lamellar bodies derived from pulmonary alveoli has been found to contain around 10% cholesterol.

The presence of sphingomyelin in natural lamellar bodies and in the synthetic lamellar bodies claimed in the present invention is important. Sphingomyelin is not generally used in liposomes and serves to give flexibility and softness to lamellar bodies. Conventional liposome technology teaches that rigidity is mandatory for the delivery of chemicals; however, we have found that flexible, low-cholesterol, sphingomyelin containing synthetic lamellar bodies are ideal for delivery of antigen to antigen presenting cells and, as demonstrated by vigorous non-receptor mediated endocytosis by dendritic cells of synthetic lamellar bodies, first described by the inventor.

Phospholipid multi-lamellar microbodies (synthetic lamellar bodies) are prepared by a technique similar to that used to produce hand-shaken multi-lamellar vesicles. The phospholipid mixture, together with cholesterol in the percentages given by weight, is dissolved in a chloroform/methanol solvent mixture (2:1 vol/vol). The lipid solution is introduced into a round-bottomed flask and attached to a rotary evaporator. The flask is evacuated and rotated at 60 r.p.m. in a thermostatically controlled waterbath at a temperature of 30° C. until a dry lipid film is deposited. Nitrogen is introduced into the flask and the residual solvent is removed before its connection to a lyophilizer where it is subjected to a high vacuum at room temperature for one hour. After release of the vacuum and following flushing with nitrogen, saline containing solutes (selected antigen) for entrapment is added. The lipid is hydrated within the flask, flushed with nitrogen, attached to the evaporator, and rotated at 60 r.p.m. at room temperature for thirty minutes. The suspension is allowed to stand for two hours at room temperature to complete the swelling process.

It should be noted that the embodiments disclosed above are merely exemplary of the invention, which may be embodied in many different forms. Therefore, details disclosed herein are not to be interpreted as limiting, but merely as a basis for Claims and for teaching one skilled in the art as to the various uses of the present invention in any appropriate manner.

Pharmaceutical Compositions and Methods of Delivery

Another aspect of the invention provides for pharmaceutical compositions comprising purified lamellar bodies for the modification of linear macromolecules. These lamellar bodies may be synthetic or naturally occurring and may act as surrogate lamellar bodies in body cavities, blood vessels, ducts, sinuses and tissues to modify mucus viscosity for therapeutic purposes.

One embodiment features treatment of a wide range of diseases and conditions with pharmaceutical compositions containing synthetic or naturally occurring lamellar bodies or microbodies and acceptable carriers and excipients. Moreover, a further embodiment may include a pharmaceutical composition designed for use in local treatment of conditions having a preponderance of heavy mucous secretions. Another embodiment may include a pharmaceutical composition designed for systemic use alone or with other standard treatment modalities known to those skilled in the art.

Such compositions comprise a therapeutically effective amount of an agent, and a pharmaceutically acceptable carrier. In one embodiment, the pharmaceutical composition may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. The unit can be, for example, a single use vial, a pre-filled syringe, a single transdermal patch and the like. The unit dosage form can be in unit dose or unit-of-use packages. As is known to those skilled in the art, a unit dose package is a convenient, patient ready unit. An exemplary unit dosage form of the present invention would be a 5 ml suspension of lamellar bodies in which there would be 54 mg of phosphatidylcholine, 19 mg of sphingomyelin, 8 mg phosphatidylethanolamine, 4 mg phosphatidylserine, 3 mg phosphatidylinosotol and 10 mg cholesterol. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Sterile isotonic aqueous buffer is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compound of the invention which will be effective in the treatment of the conditions described herein can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery or by spraying the solution containing the lamellar bodies onto the exposed tissue following surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In yet another embodiment, the lamellar bodies can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

EXAMPLES

The following examples are put forth so as to provide those of ordinary skill in the art with a complete disclosure and description of how to make and use the compositions described herein for therapeutic applications, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Ex Vivo Investigation of Effect of Synthetic Lamellar Bodies on Mucus, DNA, Actin and Alginate Gels and Ear Wax Basic laboratory bench tests have been performed on the effect on the physical properties of linear macromolecules of the type involved in the pathophysiology of secretions and exudates when mixed with phospholipid microbodies (synthetic lamellar bodies).

Materials

The materials tested were chosen in the knowledge of the probable molecular status of naturally-occurring polymers in physiologic and in pathologic conditions. The range of materials commercially available for selection was however, restricted. Nevertheless, our accumulated experience in this field directed that the main thrust of the experiments on these gel-forming polymers would be focused on demonstrating a molecular species interaction between microbodies and polymers. In this regard it was a basic premise of the experiments that the behaviour of the gels was predictably similar, because of a shared three-dimensional structure of this class of substances. Thus the selection of mucus, DNA, actin and alginate preparations were matched to the probable physical state of the polymers in vivo.

Preparation of the gels, their range of concentration and hydration was calculated to mimic as closely as possible the putative range encompassing normal and pathological conditions in humans.

Characteristics of Experimental Mucus Tested

The mucus tested was derived from bovine, submaxillary glands as supplied by Sigma (A70030). This is one of the few commercially available products whose composition is characterized. This particular agent has been tried and tested in investigation of the physical characteristics of the gel status of mucus in research on its viscosity in inflammatory respiratory disorders, including CF.

In normal secretions, e.g. upper respiratory tract surface fluid, mucus is present at low concentrations of between 0.5% and 1% by weight. 99% of the secretions consist of water containing electrolytes. Mucus has an extended polypeptide backbone (apmucin) with numerous oligosaccharide sidechains. Covered by abundant polyanionic charges, mucus, on exocytotic release from goblet cells, becomes extensively hydrated. Mucus then forms a gel whose three-dimensional structure comprises a tangled network of linear mucin polymers, devoid of intermolecular cross-bridges. In certain situations of hypersecretion and inflammation, the mucin concentration can rise to 3%-5% by weight.

Mucus has low solubility. In bench-testing of the physical properties of the bovine submaxillary mucus, solutions up to a concentration of 5% were possible using saline. For testing with lamellar bodies, concentrations at 2.5% and 3.5% were employed to mimic those encountered in pathological situations. Saline (0.9%) was used as the diluent for all mucous samples tested.

Mucin monomers are polymerized through end-to-end disulphide bonds to form linear polymers which, in respiratory mucus, are at least $30\mu$ long. These dimensions should be viewed in context of the size of lamellar bodies which range between $0.5\mu$-$2.0\mu$. Thus lamellar bodies are of a dimension which can easily pass through a tangled network of mucous "fibers" as observed by light microscopy.

Characteristics of Experimental DNA Tested

The DNA chosen was polymeric in form and derived from salmon testes (Sigma D1626). Like mucus, the DNA preparation selected consists of linear polymers which form a tangled "fibrous" gel. It is poorly soluble in water and concentrations of over 5% by weight produce a very stiff gel. In the tests carried out with lamellar bodies, concentrations of 1% were regularly employed, and the solvent used was always 0.9% saline. This concentration of 1% was selected as probably being representative of leucocyte (pus cells) and organismal-derived DNA present in thick pathological secretions in various disorders, ranging from CF through to chronic otitis media.

A 1% solution of polymeric DNA in physiological saline is a clear, syrupy liquid whose gel state possesses high viscosity and adhesiveness.

Characteristics of Experimental Combined Mucus and DNA Gels

Solutions of 2.5% mucus in 0.9% saline and 1% DNA in 0.9% saline were made up separately. They were then carefully mixed and stirred, avoiding the creation of bubbles. The gels mixed well, without producing any changes in turbidity. It is noteworthy that in published studies, samples from patients of thick, viscous, infected respiratory mucus when stained for DNA and mucus, showed in wet preparations examined by confocal microscopy that the different polymers were intimately mixed in the three-dimensional structure of the gel. We were therefore confident that the samples of combined mucus and DNA gel prepared for testing with lamellar bodies were most probably representative of viscous effusions in pathological situations in a variety of in vivo disorders, ranging from CF through to chronic otitis media.

Characteristics of Synthetic Lamellar Bodies

The lamellar bodies tested were produced by the mixing of two organic solvents containing the phospholipids and cholesterol components. Based on analysis of lamellar bodies produced by human mesothelial cells, six constituents (five phospholipids and cholesterol) are used to make microbodies consisting of tightly-packed phospholipid bilayers with an ultrastructural geometry and periodicity (distance between bilayers) confirmed by electron microscopy to be identical to that of naturally—occurring lamellar bodies. The range of size of the synthetic lamellar bodies (0.2-3.5 µm) was closely similar to that found in tissues and body cavities in man.

The lamellar bodies are made up in a physiological saline to a standard solution containing $10 \times 10^9$ microbodies per ml. The lamellar body density estimates are checked by turbidity comparison methods, while size distribution is obtained using flow cytometry.

Methods

Considering the widespread occurrence of mucus throughout the body, the literature on experimental work on its molecular biology is surprisingly scant. Current literature on the pathogenesis of cystic fibrosis admits ignorance of the basic pathogenetic mechanisms pertaining to mucus in different disorders. It is agreed by those in this field that investigation of visco-elastic properties of biological fluids and gels poses many technical and instrumental difficulties.

Applied viscometry has been developed exclusively for industrial purposes, and all instruments are designed for large fluid volumes. Pure biological polymers are extremely expensive and measurement of multiple samples, where minimal testing volumes per sample on available instruments are 10-20 ml, can be prohibitive.

Standard industrial viscometers employ mechanical techniques, inducing shears, causing alignment of linear polymers and thus disentangling the gel. Therefore, measurement of biological gels in standard viscometers (e.g. rotating disc and cone) can significantly alter the viscosity of the sample during the test. On the other hand, rheology of biological fluids has evolved using instruments for investigation of blood which is a non-Newtonian fluid. Likewise plasma viscosity is highly dependent on globular, not linear, proteins like albumin at 45 g/l and globulin at 35 g/l. Only one company (recently disbanded) has designed instruments for measurement of viscosity in biological fluids.

To obviate the difficulties in using instruments not modified for testing viscosity in biological samples, a series of pilot studies were carried out employing simple devices to identify the most suitable method for providing reliable measurements of change in viscosity in gels mixed in saline with and without added lamellar bodies.

A method was developed which measured distance travelled in unit time by fixed volumes of test and control samples, down a fixed incline under gravity (Galileo technique), where the density and water content of the samples were comparable, and the surface chosen was of homogeneous composition, surface texture and charge. The most appropriate slope tested was the surface of a plastic Petri dish.

All laboratory ware used (i.e. containers, pipettes, etc) were of plastics which did not contain plasticisers of the type DEHP, since lamellar bodies leach out and are altered by this plasticiser.

Gels were freshly made up to the appropriate concentrations with adequate and careful mixing, ensuring complete solubility and hydration of the polymers.

A measured volume of 0.9% saline containing lamellar bodies was then added to test samples and an identical volume of 0.9% saline only was added to the control samples. Following careful, but complete mixing, samples were incubated at 37° C. for 1 hour.

After incubation and further careful mixing, droplets (ranging from 30 µl-100 µl) were accurately pipetted on a start-line marked on the back of the Petri dish, which also had a parallel "finish" line drawn at a distance of 5 cms. As the Petri dish was elevated to an angle of 90°, an electronic stopwatch was triggered which was used to record by observation the time taken for the droplet to stream down to the 5 cm marker.

Results

The key elements of the findings are summarized in Tables 1-3, described below.

Table 1. Effect of varying concentrations of synthetic lamellar bodies on mucus fluidity compared with use of saline diluent as control. Each sample tested was exactly 30 µl. The angle of incline was 90°.

Table 2. Effect at 37° C. of varying concentrations of synthetic lamellar bodies on DNA fluidity compared with use of saline diluent as control. Each sample tested was 100 µl. The angle of incline was 90°.

Table 3. Effect at 37° C. of synthetic lamellar bodies on fluidity of a combined mucus—DNA gel at a ratio of one third volume synthetic lamellar bodies to two thirds DNA & mucus gel compared with control using one third volume of 0.9% saline. Each sample tested was 40 µl. The angle of incline was 90°.

Effect of Varying Concentrations of Lamellar Bodies on Mucus Gels

The experiment most representative of the alterations observed in the viscosity of mucus was the one illustrated in Table 1 in which 3.5% mucus in saline was sequentially diluted with increasing volumes of 0.9% saline (controls) and 0.9% saline containing $10\times10^9$ lamellar bodies. The ratios of gel to diluent tested for both test and control samples were 19:1, 9:1, 8:2, 7:3, 6:4.

No movement was observed in any of the samples in which the diluent mixed with the mucus gel was physiological saline only, in contrast to the test samples in which the saline diluent contained lamellar bodies, where even at a ratio of 19:1 there was significant movement in the solution down the inclined plane. Thereafter, the speed of travel increased steeply and at the ratio of nine parts mucus to one part lamellar body solution, the fluid travelled five centimeters in six seconds. At ratios of seven parts to three, a maximum speed of travel was reached at five centimeters per second. At these concentrations the tests demonstrated highly significant differences in the behavior between the mucus gels mixed with matched volumes of saline alone, compared with test samples where the saline contained lamellar bodies. These results tested within the stated range and concentrations demonstrate that the presence of the phospholipid microbodies confer a remarkable lubricity to the gel, independent of the fluid content of the diluent.

Effect of Varying Concentrations of Lamellar Bodies on DNA Gels

The experiment most representative of the alterations observed in the viscosity of DNA was the one illustrated in Table 2, one in which 1% DNA in saline was sequentially diluted with increasing volumes of 0.9% saline (controls) and 0.9% saline containing $10\times10^9$ lamellar bodies. The ratios of gel to diluent tested for both test and control samples were 19:1, 9:1, 8:2, 7:3, 6:4, 5:5. Minimal movement was observed in both test and control at dilutions from 19:1 down to 8:2. Thereafter, test samples in which the diluent contained lamellar bodies in ratios of 7:3, 6:4, 5:5 exhibited a steep increase in speed of travel to 2.5 cms per second, as compared to controls where the maximum speed was 5 cms in 4 min 20 sec.

Effect of Varying Concentrations of Lamellar Bodies on Combined DNA & Mucus Gels The experiment most representative of the alterations observed in the viscosity of combined DNA and mucus gels was the one illustrated in Table 3. The combined gel consisted of 333 µl of 2.5% mucus in 0.9% saline, together with 333 µl of 1% DNA in 0.9% saline. In the control sample 333 µl of 0.9% saline was added as diluent, whereas in the test sample 333 µl of saline containing $10\times10^9$ lamellar bodies was added to the combined gel. No movement was obtained in the control sample, whereas the test sample containing lamellar bodies travelled 5 cms in 2 sec at a speed of 2.5 cms per sec. Therefore at a ratio of one third diluent containing lamellar bodies added to two thirds combined mucus and DNA gel, there was complete contrast between the fluidity of the control and test sample.

Alginate and Actin Gels

Broadly similar results as those found in the testing of the effect of lamellar bodies on mucus and DNA were obtained in comparing their effect on alginate and actin gels. The agents tested were muscle-derived, porcine actin G (Sigma A0541) made up as a 0.5% solution in 0.9% saline. Alginic acid, a polyuronic acid composed primarily of anhydro-beta-D mannuronic acid residues with 1-4 linkage (Sigma A70030) was made up as a 2.5% solution in 0.9% saline. Light microscopic observations showed intimate mixing of lamellar bodies between the "fibers" of the gels.

Effect of Lamellar Bodies on Mucus Plugs Blocking Tympanostomy Tubes (Vent Tubes)

In vitro laboratory experiments were carried out in which vent tubes were filled with 5% mucus gel and allowed to dry overnight. The tubes were inserted in the spigot of a specially chosen 2 ml syringe, whose conical profile accommodated precisely the outer diameter of the vent tube, to achieve complete occlusion. 0.5 ml suspension of lamellar bodies was pipetted into the barrel of the syringe and its effect observed. Vent tubes were unplugged at room temperature in a period that ranged from 30-60 minutes. Saline controls had no effect after 6 hours.

Effect of Lamellar Bodies on Ear Wax

Human ear wax is a mixture of substances. The two main constituents are desquamated squamous cells and cerumen.

The squamous epithelium which lines the external auditory canal occupies an unusual position for skin. Over the rest of the body the epidermis is renewed by constant loss of surface cells and keratin by abrasion. Loss by abrasion is not possible in the auditory canal. To overcome this difficulty the surface epithelium continually migrates centrifugally from the eardrum outwards. Cerumen is a waxy secreted by modified sweat glands. These are situated in the sub-epidermal tissue from where they discharge their secretion through ducts onto the surface of the external auditory canal.

We have carried out tests in the laboratory on the effect of lamellar bodies on samples of wax obtained from patients, and have shown that the wax disintegrates over a period ranging from 12-24 hours. Microscopic observations on the process show penetration between the plates of squames by lamellar bodies, lubricating and separating the adhesive layers of dead cells which led to disintegration of the wax.

Conclusions

The mixing of a saline solution containing lamellar bodies with a mucus gel results in significant reduction in the adhesiveness and viscosity of the mixture, compared to a control mucus gel which has been mixed with an equal volume of saline alone, when measured by rate of movement down an inclined plane of identical composition, surface texture and charge. Similar results were obtained when lamellar bodies were added to DNA, actin and alginate gels, and also to combined mucus and DNA gels. Significant changes in speed of flow, and hence fluidity, were encountered when the ratio of the volume of standard solution containing lamellar bodies added to the gel was around 3 to 7.

TABLE 1

Effect of varying concentrations of synthetic lamellar bodies on mucus fluidity compared with use of saline diluent as control. Each sample tested was exactly 30 µl. The angle of incline was 90°.

| CONTROL 3.5% Mucus in 0.9% saline:saline diluent 0.9% saline | | | TEST 3.5% Mucus in 0.9% saline:Synthetic lamellar bodies in 0.9% saline | | |
|---|---|---|---|---|---|
| Volume & Concentration | Dilution | Time to Travel 5 cms | Dilution | Volume & Concentration | |
| 950 µl mucus + 50 µl NaCl | 19:1 | No movement @ 5 min | 3 m 50 sec | 19:1 | 950 µl mucus + 50 µl LMS |
| 900 µl mucus + 100 µl NaCl | 9:1 | No movement @ 5 min | 6 sec | 9:1 | 900 µl mucus + 100 µl LMS |
| 800 µl mucus + 200 µl NaCl | 8:2 | No movement @ 5 min | 2 sec | 8:2 | 800 µl mucus + 200 µl LMS |
| 700 µl mucus + 300 µl NaCl | 7:3 | No movement @ 5 min | 1 sec | 7:3 | 700 µl mucus + 300 µl LMS |
| 600 µl mucus + 400 µl NaCl | 6:4 | No movement @ 5 min | 1 sec | 6:4 | 600 µl mucus + 400 µl LMS |

TABLE 2

Effect at 37° C. of varying concentrations of synthetic lamellar bodies on DNA fluidity compared with use of saline diluent as control. Each sample tested was 100 µl. The angle of incline was 90°.

| CONTROL 1% DNA in 0.9% saline:diluent 0.9% saline | | | TEST 1% DNA IN 0.9% saline:Synthetic lamellar bodies in 0.9% saline | | |
|---|---|---|---|---|---|
| Volume & Concentration | Dilution | Time to Travel 5 cms | | Dilution | Volume & Concentration |
| 950 µl DNA + 50 µl NaCl | 19:1 | 10 mm @ 5 min | 11 mm @ 5 min | 19:1 | 950 µl DNA + 50 µl LMS |
| 900 µl DNA + 100 µl NaCl | 9:1 | 10 mm @ 5 min | 11 mm @ 5 min | 9:1 | 900 µl DNA + 100 µl LMS |
| 800 µl DNA + 200 µl NaCl | 8:2 | 25 mm @ 5 min | 31 mm @ 5 min | 8:2 | 800 µl DNA + 200 µl LMS |
| 700 µl DNA + 300 µl NaCl | 7:3 | 45 mm @ 5 min | 22 sec | 7:3 | 700 µl DNA + 300 µl LMS |
| 600 µl DNA + 400 µl NaCl | 6:4 | 4 min 20 sec | 2 sec | 6:4 | 600 µl DNA + 400 µl LMS |
| 500 µl DNA + 500 µl NaCl | 5:5 | 2 min 32 sec | 2 sec | 5:5 | 500 µl DNA + 500 µl LMS |

TABLE 3

Effect at 37° C. of synthetic lamellar bodies on fluidity of a combined mucus - DNA gel at a ratio of one third volume synthetic lamellar bodies to two thirds DNA & mucus gel compared with control using one third volume of 0.9% saline. Each sample tested was 40 µl. The angle of incline was 90°.

| CONTROL | TIME TO TRAVEL 5 CMS | | TEST |
|---|---|---|---|
| 333 µl 2.5% mucus in 0.9% saline 333 µl 1% DNA in 0.9% saline 333 µl 0.9% saline as diluent | No movement @ 5 min | 2 sec | 333 µl 2.5% mucus in 0.9% saline 333 µl 1% DNA in 0.9% saline 333 µl LMS in 0.9% saline |

What is claimed is:

1. A method for increasing the fluidity of a subject's surface airway surface fluid and restoring mucociliary clearance of secretions of the respiratory tract comprising applying an aerosol composition comprising lamellar bodies, wherein said lamellar bodies comprise phosphatidylcholine, sphingomyelin, phosphatidyl ethanolamine, phosphatidyl serine, phosphatidyl inositol and cholesterol, wherein said lamellar bodies are phospholipid multilamellar bilayered structures which comprise about 44-70% phosphatidylcholine, about 15-23% sphingomyelin, about 6-10% phosphatidyl ethanolamine, about 2-6% phosphatidyl serine, about 2-4% phosphatidyl inositol and about 4-12% cholesterol by weight to a subject's respiratory passages to modify the physical properties of linear macromolecules of the type mucous DNA, actin and alginate in pathologically altered secretions, wherein the pathologically altered secretions are present in a condition selected from the group consisting of cystic fibrosis, bronchiectasis, chronic obstructive pulmonary disease and nasal congestion.

2. The method of claim 1 wherein the composition contains suspended lamellar bodies wherein the method includes the step of administering the suspended lamellar bodies into the respiratory passages as an aerosol spray.

3. The method of claim 1 wherein the lamellar bodies comprise about 54% phosphatidylcholine, about 19% sphingomyelin, about 8% phosphatidyl ethanolamine, about 4% phosphatidyl serine, about 3% phosphatidyl inositol and about 10% cholesterol by weight.

4. The method of claim 1 wherein the lamellar bodies further comprise about 0-3% by weight of lysophosphatidyl choline.

5. The method of claim 1 wherein the lamellar bodies further comprise about 2% by weight of lysophosphotidyl choline.

* * * * *

UNITED STATES PATENT AND TRADEMARK OFFICE
CERTIFICATE OF CORRECTION

| | | |
|---|---|---|
| PATENT NO. | : 9,173,901 B2 | Page 1 of 1 |
| APPLICATION NO. | : 12/313724 | |
| DATED | : November 3, 2015 | |
| INVENTOR(S) | : James Dobbie | |

It is certified that error appears in the above-identified patent and that said Letters Patent is hereby corrected as shown below:

On the Title page, left column, under Assignee, (73) delete "LAMELLAR THERAPEUTICS LIMITED", and insert --LAMELLAR BIOMEDICAL LIMITED--.

Signed and Sealed this
First Day of March, 2016

Michelle K. Lee
*Director of the United States Patent and Trademark Office*